United States Patent
De Angeli

(10) Patent No.: US 10,585,064 B2
(45) Date of Patent: Mar. 10, 2020

(54) WIRELESS PH AND TEMPERATURE SENSOR FOR CHEMICAL CONTAINERS

(71) Applicant: Marco De Angeli, Barzana (IT)

(72) Inventor: Marco De Angeli, Barzana (IT)

(73) Assignee: FLEX LTD., Singapore (SG)

( * ) Notice: Subject to any disclaimer, the term of this patent is extended or adjusted under 35 U.S.C. 154(b) by 136 days.

(21) Appl. No.: 15/908,380

(22) Filed: Feb. 28, 2018

(65) Prior Publication Data

US 2019/0265192 A1    Aug. 29, 2019

(51) Int. Cl.
*G01N 27/416*    (2006.01)
*H04B 5/00*    (2006.01)

(52) U.S. Cl.
CPC ....... *G01N 27/4167* (2013.01); *H04B 5/0043* (2013.01)

(58) Field of Classification Search
CPC .......... G01W 1/16; G01W 1/10; G01R 27/28; G01R 29/26; G01R 29/0842; H04B 1/1027; H04B 5/0043; G01N 27/4167
USPC ................ 324/620, 346, 333, 334, 338, 339
See application file for complete search history.

(56) References Cited

U.S. PATENT DOCUMENTS

| | | | |
|---|---|---|---|
| 9,987,900 B2 * | 6/2018 | Farjoud | B60G 17/08 |
| 2014/0163476 A1 * | 6/2014 | Chevallier | A61M 5/326 604/198 |
| 2018/0021604 A1 * | 1/2018 | Hansen | A62B 3/005 |

* cited by examiner

*Primary Examiner* — Giovanni Astacio-Oquendo
(74) *Attorney, Agent, or Firm* — Volpe and Koenig, PC

(57) ABSTRACT

Described herein is a method for and a device configured to receive a magnetic filed at a near field communication (NFC) tag, generate energy via induction from the magnetic field, and activate a temperature sensor form at least a portion of the generated energy. An electrochemical sensor may be activated from a portion of the generated energy and a temperature value of a container, solution and/or a housing may be measured based on thermal conduction such that the temperature value is measured using a temperature sensor. A pH value may be measured using an electrochemical sensor. The temperature value may be transmitted to a first receiver using at least a portion of the generated energy and the pH value may be transmitted to a second receiver.

20 Claims, 5 Drawing Sheets

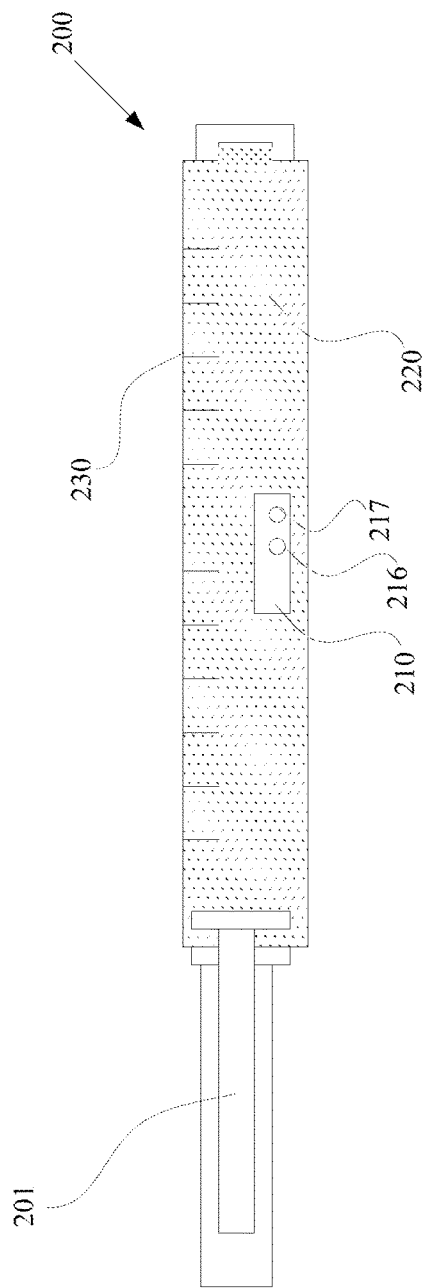
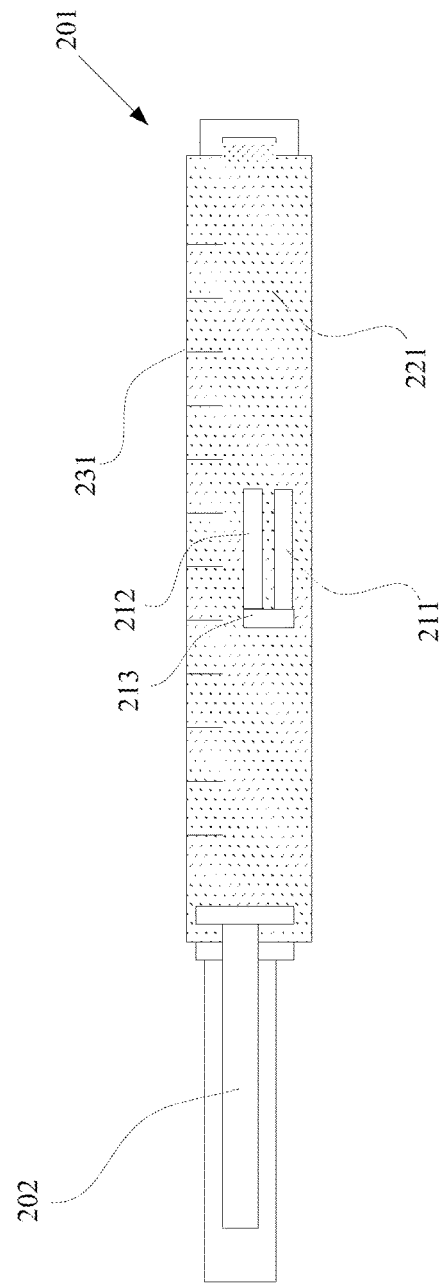
FIG. 2a
FIG. 2b

US 10,585,064 B2

WIRELESS PH AND TEMPERATURE SENSOR FOR CHEMICAL CONTAINERS

BACKGROUND

Chemical containers such as vials that contain drug solutions are often placed in storage until they need to be used. While stored, the certain properties, such as the temperature, must be maintained to ensure that the solution can be used safely and remains effective.

Use of a solution that is stored in a container may also require determining characteristics of the solution, prior to use, such that the solution can only be used when one or more characteristics reach respective threshold values. Accordingly, such characteristic values must be obtained in an efficient and cost effective manner.

SUMMARY

In an aspect, the invention relates to a method for and a system to receive a magnetic field at a near field communication (NFC) tag, generate energy via induction from the magnetic field, and activate a temperature sensor form at least a portion of the generated energy. An electrochemical sensor may also be activated from a portion of the generated energy and a temperature value of a container, solution and/or a housing may be measured based on thermal conduction such that the temperature value is measured using a temperature sensor. A pH value may be measured using an electrochemical sensor. The temperature value may be transmitted to a first receiver using at least a portion of the generated energy and the pH value may be transmitted to a second receiver using at least a portion of the generated energy.

In an aspect, the invention relates to a Near Field Communications (NFC) tag device with a housing. A temperature sensor may be at least partially contained in the housing and configured to measure a temperature value of a container, a solution, or the housing such that the temperature sensor measures the temperature value based on thermal conduction. An electrochemical sensor may be at least partially contained in the housing and configured to measure a pH value. The NFC tag may be configured to transmit a temperature signal including the temperature value, to a first receiver and may be configured to transmit a pH signal including the pH value to a second receiver.

BRIEF DESCRIPTION OF THE DRAWINGS

A more detailed understanding may be had from the following description, given by way of example in conjunction with the accompanying drawings wherein:

FIG. 2a is diagram of a solution container with sensors;

FIG. 2b is diagram of another solution container with sensors;

DETAILED DESCRIPTION OF EMBODIMENTS

Figure 1:
FIG. 1 is a flowchart detailing a method for transmitting a temperature value and a pH value.

Examples of different sensor and transmitting device implementations will be described more fully hereinafter with reference to the accompanying drawings. These examples are not mutually exclusive, and features found in one example can be combined with features found in one or more other examples to achieve additional implementations. Accordingly, it will be understood that the examples shown in the accompanying drawings are provided for illustrative purposes only and they are not intended to limit the disclosure in any way. Like numbers refer to like elements throughout.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present invention. As used herein, the term "and/or" includes any and all combinations of one or more of the associated listed items.

It will be understood that when an element such as a layer, region or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. It will be understood that these terms are intended to encompass different orientations of the element in addition to any orientation depicted in the figures.

Relative terms such as "below" or "above" or "upper" or "lower" or "horizontal" or "vertical" may be used herein to describe a relationship of one element, layer or region to another element, layer or region as illustrated in the figures. It will be understood that these terms are intended to encompass different orientations of the device in addition to the orientation depicted in the figures.

As disclosed herein, a container may be any shape or size configured to hold a solution such as a medical drug. The container may be spherical, cylindrical, rectangular, or any other shape. The container may be made of material configured to contain a solution within the container such as, but not limited to, glass, plastic, metal, a combination thereof or a combination of two or more materials, or the like. As shown in the examples described herein, the container may be an auto-injector where a drug vial is placed in the auto-injector to be used during a medical procedure.

As disclosed herein, a solution may be any solution that is capable of existing in a liquid form at a given temperature. The solution may be, but is not limited to, a medical drug, a chemical, a vaccine, a surgical solution, or the like or a combination thereof.

FIG. 1 shows a method 100 to transmit data collected via one or more sensors. At step 110 a magnetic field may be received at a Near Field Communication (NFC) tag. As further discussed herein, a magnetic field may be provided by any device configured to transmit a magnetic field such as, for example, a mobile phone. The magnetic field may be provided to the NFC tag as a result of the device transmitting the magnetic field being proximal to the NFC tag. As further discussed herein, an NFC tag may be any applicable tag configured to generate energy and activate based on receiving an energy field, such as a magnetic field. At step 120, energy may be generated at the NFC tag via induction from the magnetic field. As further discussed herein, the energy may be generated via the interaction of the magnetic field with coils contained in the NFC tag.

At step 130 a temperature sensor may be activated using the energy generated at step 120. The temperature sensor may be part of or in connection with the NFC tag and may use part of the energy generated at step 120 for activation. At step 140 an electrochemical sensor may be activated using the energy generated at step 120 or may be self-energized. The electrochemical sensor may be part of or in connection with the NFC tag and may use part of the energy generated at step 120 for activation.

At step 150, the temperature sensor may measure a temperature value via thermal conduction. The temperature value may correspond to the temperature of the container or the temperature of the solution within the container, as further disclosed herein. At step 160, the electrochemical sensor may measure a pH value. The pH value may correspond to the pH value of the solution within the container or the pH value at the sensor itself, as further disclosed herein.

At step 170, the temperature value may be transmitted to a first receiver using a portion of the energy generated at step 120. At step 180, the pH value may be transmitted to a second receiver using a portion of the energy generated at step 120. The first and the second receiver may be the same receiver such as, for example, a cellular phone. Notably, based on method 100, both a temperature value and a pH value may be transmitted via an NFC tag. FIGS. 2A and 2B show example configurations of a container with an NFC tag configured in accordance with the techniques disclosed herein and further discussed below.

Figure 3:
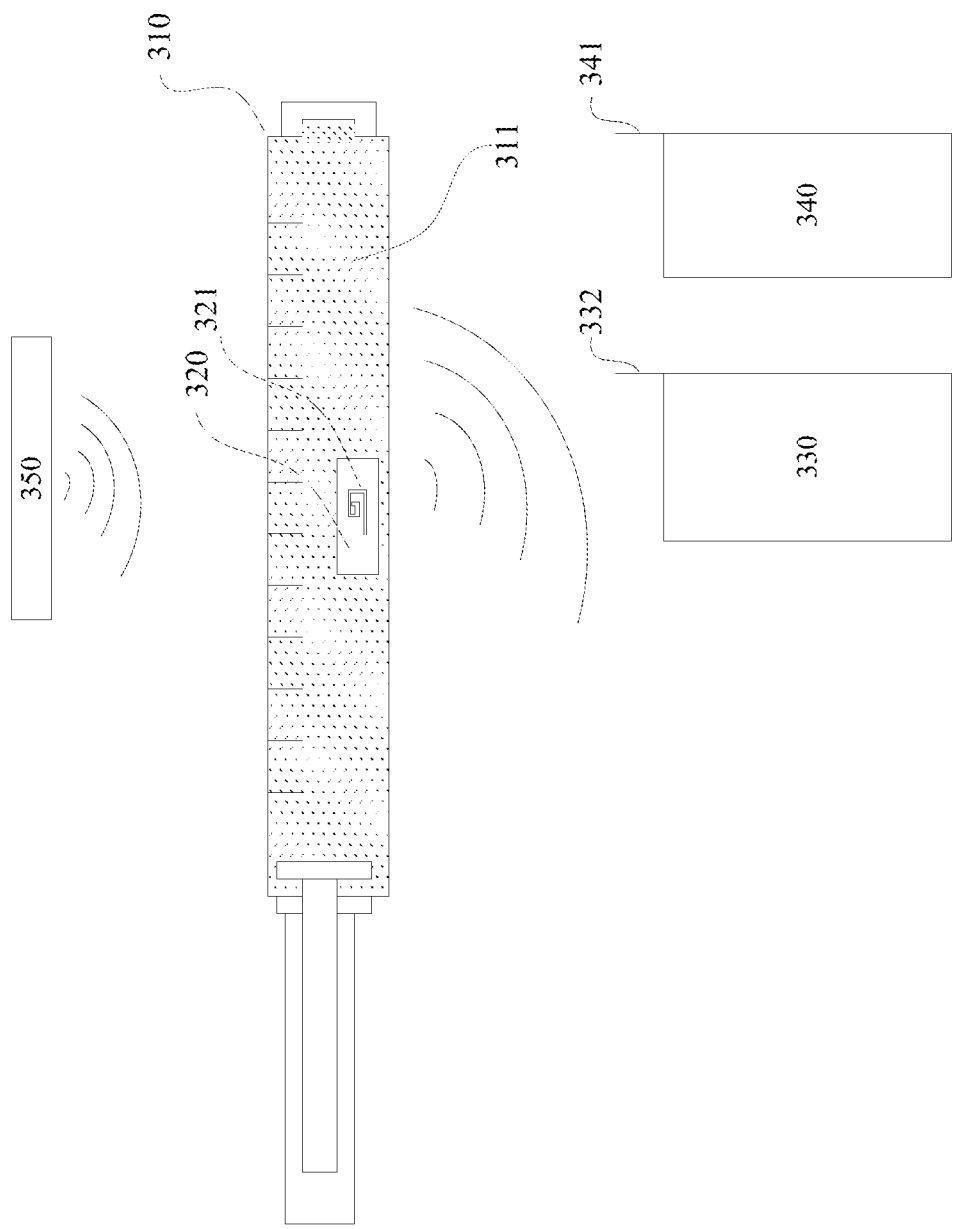
FIG. 3 is a diagram of a solution container receiving and transmitting wirelessly.
Figure 4:
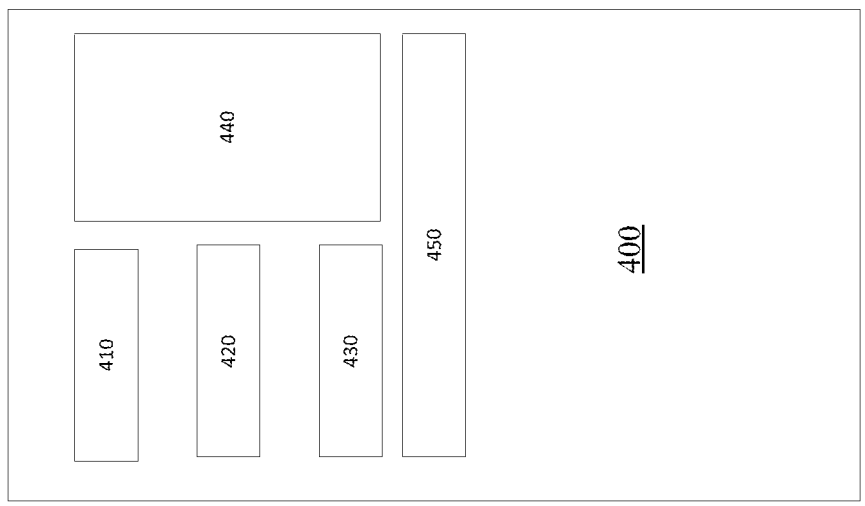
FIG. 4 is a diagram of a receiver receiving sensor data.
Figure 5:
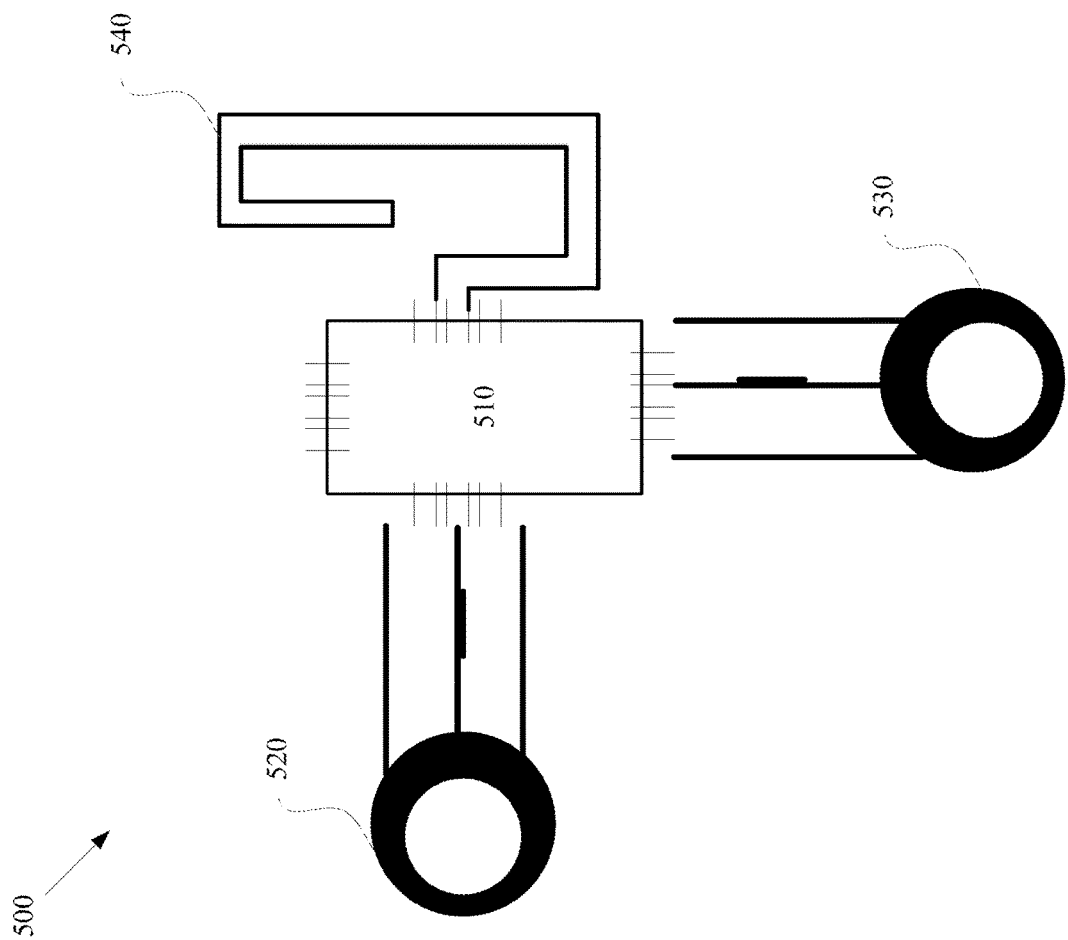
FIG. 5 is a diagram of a NFC tag attached to a temperature sensor, an electrochemical sensor and an antenna.

At step 110 of method 100 in FIG. 1, a magnetic field may be received at an NFC tag. It will be understood that although an NFC tag is specifically disclosed herein, an NFC tag may refer to any near field communication component such as, for example, a Radio Frequency Identification component. An NFC tag may be any applicable shape and size and may be contained in a thin laminate housing that can be applied to, for example, the curved glass surface of a container. An NFC tag may be secured to a container in any applicable manner such as via an adhesive, a binding tape, a suction element, or a mechanical connection. A mechanical connection may include securing an NFC tag to a container such that the container is manufactured to include the NFC tag or to have the NFC tag inserted such as, for example, an NFC tag inserted into an injection molded plastic. As an example, the NFC tag may contain a top surface and a bottom surface such that the bottom surface has an adhesive layer. The adhesive layer may attach the NFC tag to a container. The magnetic field may be generated via any applicable device such as a standalone component configured to provide such magnetic fields proximal to one or multiple containers within a storage unit, a mobile device such as a cellular phone which is proximal to a container, or the like. The magnetic field may induce a current within the NFC tag via, for example, a set of coils contained within the NFC tag. FIG. 3 shows an example system with NFC tag 320 including antenna 321 which may contain said set of coils. A standalone component 350 may generate a magnetic field proximal to the container 310. The magnetic field may be received at coils in the antenna 321 of a NFC tag 320 such that an induced current is generated and the antenna 321 may also be used to transmit a signal to one or more receivers such as receivers 330 and 340 of FIG. 3 and as further described in FIG. 4 herein. As another example, FIG. 5 shows a NFC tag 500, which includes a controller 510, temperature sensor 520, electrochemical sensor 530 and antenna 540. The antenna 540 may include coils such that a magnetic field proximal to the antenna 540 may induce a current within antenna 540.

At step 120 of method 100 in FIG. 1, the induced current may provide energy to be used by the components of the NFC tag such as by the temperature sensor and/or electrochemical sensor. As shown in FIG. 5, the energy provided via the antenna 540 may be transferred to the controller 510. The controller 510 may further distribute the energy to components such as the temperature sensor 520 and electrochemical sensor 530.

At step 130 of method 100 in FIG. 1, a temperature sensor, such as temperature sensor 520 of FIG. 5, may be activated from a portion of the generated energy. The activation of the temperature sensor 520 may enable the temperature sensor 520 to sense temperatures via, for example, thermal conduction. The temperature sensor 520 may be configured such that its sensing components are in contact with the container and, accordingly, any temperature values determined by the temperature sensor 520 correspond to the temperature of the container. Alternatively, the temperature sensor 520 may be configured such that all or parts of its sensing components are in contact with the solution via, for example, an opening in the container. Accordingly, any temperature values determined by the temperature sensor 520, with such a configuration, correspond to the temperature of the solution.

At step 140 of method 100 in FIG. 1, an electrochemical sensor, such as electrochemical sensor 530 of FIG. 5, may be activated. The sensor may be self-energy sufficient or may be activated using a portion of the generated energy. The activation of the electrochemical sensor 530 may enable the electrochemical sensor 530 to sense a pH value. The electrochemical sensor 530 may be configured such that its sensing components are in contact with the container and, accordingly, any pH values determined by the electrochemical sensor 530 correspond to the pH on the surface of the container. Alternatively, the electrochemical sensor 530 may be configured such that all or parts of its sensing components are in contact with the solution via, for example, an opening in the container. Accordingly, any pH values determined by the electrochemical sensor 530, with such a configuration, correspond to the pH of the solution within the container.

At step 150 of method 100 in FIG. 1, the temperature sensor 520 of FIG. 5 may be configured to sense the temperature of either the housing of a container that contains a solution or may be configured to sense the temperature value of the solution itself. The temperature sensor 520 may be configured to sense the temperature value based on temperature change in electrical circuits within the temperature sensor 520. The temperature value may be read from these sensors by taking measurements of the voltage outputs of the circuits. Alternatively, a temperature sensor 520 may have a predictable resistance that is affected by temperature change such that the temperature value may be determined as either the electrical current in the temperature sensor 520 changes or as the resistance within the temperature sensor 520 increases and/or decreases. Electrical current or resistance changes may be mapped using a predetermined formula to determine a temperature value. It will be understood that if the temperature sensor 520 determines the temperature value of the solution, the opening or other mechanism to reach the solution via the container may be configured such that solution does not flow out of such an opening or mechanism.

At step 160 of method 100 in FIG. 1, the electrochemical sensor 530 of FIG. 5, may be configured to sense the pH value at either the housing of a container that contains a solution or may be configured to sense the pH value of the solution itself. The electrochemical sensor 530 may be configured to sense the pH value based on any applicable technique including, for example, by sensing a potential related to a hydrogen ion concentration within the solution. An electrochemical sensor 530 configured to measure the pH value at the surface of the container may be attached to the container with its sensing components in contact with or proximal to the surface of the container. An electrochemical sensor 530 configured to measure the pH value of the solution may contain sensing components that are in contact with the solution via the container such as via openings in the container that allow such sensing components to reach the solution. It will be understood that if the electrochemical sensor 530 determines the pH value of the solution, the opening or other mechanism to reach the solution via the container may be configured such that solution does not flow out of such an opening or mechanism.

At step 170 of method 100 in FIG. 1, the temperature value measured by the temperature sensor 520 of FIG. 5 is transmitted to a first receiver. An example configuration is illustrated in FIG. 3. As shown, the NFC tag 320 may contain a temperature sensor which measures a temperature value. The temperature value may be wirelessly transmitted to a first receiver 330 via its antenna 332. A portion of the energy generated at step 120 may be used to transmit the temperature value from a NFC tag such as NFC tag 320 of FIG. 3 or via the NFC tag controller 510 of FIG. 5. The transmission may occur such that the first receiver 330 of FIG. 3 is within a proximal distance to the NFC tag 320 of FIG. 3, or 510 of FIG. 5, and such that the transmission is facilitated using NFC/RFID techniques. According to an implementation, the temperature value may be transmitted to an intermediate device such that the intermediate device is configured to further transmit the temperature value using a powered format such as over Wi-Fi, infrared, cellular, or via Bluetooth® technology.

At step 180 of method 100 in FIG. 1, the pH value measured by the electrochemical sensor 530 is transmitted to a first receiver. A portion of the energy generated at step 120 is used to transmit the temperature value. The transmission may occur such that the receiver is within a proximal distance to the NFC tag and such that the transmission is facilitated using NFC/RFID techniques. The temperature value may be transmitted to an intermediate device such that the intermediate device is configured to further transmit the temperature value using a powered format such as over Wi-Fi, infrared, cellular, or via Bluetooth® technology.

Notably, as disclosed via method 100 of FIG. 1, a non-powered NFC tag may receive a magnetic field and generate energy to measure a temperature value and a pH value and further to transmit the temperature value and pH value to one or more receivers. As show in FIG. 5, an NFC tag 500 may also contain a controller 510 that contains a storage component. The storage component may store information such as previous temperature values, previous pH values, manufacturing parameters, drug parameters, production dates, expiration date, lot numbers, date of last use, or the like. One or more of such information may be transmitted, by the NFC tag 500, to one or more receivers during operation of the NFC tag 500.

FIGS. 2a and 2b show auto-injector containers 200 and 201 configured in accordance with the subject matter disclosed herein. As shown in FIG. 2a, an auto-injector container 200 may include a vial 230, with a solution 220 and an extraction mechanism such as a push nob 201. A housing for NFC tag 210 may include an antenna (not shown), a temperature sensor 216 and an electrochemical sensor 217. Alternatively, FIG. 2b shows an auto-injector container 201 that may include a vial 231, with a solution 221 and an extraction mechanism such as a push nob 202. An NFC controller 213 may be configured to receive a magnetic field and generate energy using the magnetic field. The energy may be provided to a temperature sensor 212 and an electrochemical sensor 211. Note that although FIGS. 2a and 2b provide two example configurations of an NFC tag with a temperature and electrochemical sensor, it should be noted that additional configurations may be used to implement the techniques disclosed herein.

As an example implementation of the techniques disclosed herein, the configuration of FIG. 3 may be used to alert medical professionals that solution 311 within a container 310 is at an optimal state for use. The container 310 may be removed from a storage device (not shown) that is configured to keep the container and respective solution 311 at a storage temperature that is lower than the optimal state temperature. The solution 311 may be most effective when used at the optimal state temp. A standalone device 350 may periodically provide the NFC tag 320 with a magnetic field such that the magnetic field is received at the antenna 321 and energy is provided a temperature and an electrochemical sensor (not shown) housed in the NFC tag 320. The temperature sensor may measure a temperature value of the container 310 and the NFC tag 320 may transmit the temperature value to a first receiver 330 configured to receive the temperature value via antenna 332. The first receiver 330 may be configured to alert a user, such as a medical professional when the temperature value of the container 310, as provided by the NFC tag 320, reaches the optimal state temperature. Additionally, the electrochemical sensor may measure a pH value at the container 310 and the NFC tag 320 may transmit the pH value to a second device 340 configured to receive the pH value via antenna 341. If a pH value corresponding to condensation or expected room humidity is received at the second device 340, the device may either report the value via second receiver 340 or may not take any action. If the pH value falls outside an expected condensation or room humidity pH value, then the second receiver may signal an alert or warning sign indicating that either the solution within the container 310 leaked out or that an external solution is disposed on the surface of the container 310.

It will be noted that standalone device 350, first receiver 330, and second receiver 341 may all be the same device or one or more combinations of the three may be included in a single device. As an example, the first receiver 330 and second receiver 340 may be the same device such as cellular phone 400, as shown in FIG. 4. Cellular phone 400 may include an application that can be activated by a user. The application may provide information via a number of fields such as temperature value field 410, pH value field 420, estimated time to optimal state temperature field 430, optimal state ready indication field 450, and warning indication field 440. The temperature value field 410 may provide the last received temperature value from an NFC tag and may initiate a new reading based on user input within the application on cellular phone 400. The pH value field 410 may provide the last received pH value from an NFC tag and may initiate a new reading based on user input within the application on cellular phone 400. The estimated time to optimal state temperature field 430 may provide estimated time duration for the temperature value of the container or solution to reach an optimal state temperature. The estimated time duration may, for example, enable a medical professional to coordinate use of solution within a container with other medical activities and optimize the use of the solution during a procedure. The optimal state ready indication field 450 may provide a positive indication such as, for example, a green icon, which says "OK For Use" when, at least, the temperature value is at an optimal state temperature and the pH value does not indicate a leak or spill. The warning indication field 440 may provide a negative indication such as, for example, a red icon, which says "Not OK For Use" when ether the temperature value is not within an optimal state temperature range or when the pH value indicates a leak or spill.

As another example implementation of the techniques disclosed herein, the configuration of FIG. 3 may be used to provide an alert that indicates that solution 311 within a container 310 is no longer fit for use or require an evaluation to determine whether container 310 is fit for use. The standalone device 350 may periodically provide a magnetic field to NFC tag 320 and NFC tag 320 may transmit a temperature value and pH value in accordance with the techniques disclosed herein. If a first receiver 330 receives a temperature value that is outside an acceptable storage temperature value range, the receiver 330 may provide an alert to a user or to a system configured to receive such alerts. Based on the alert, a user or system may adjust a temperature setting to bring the temperature of the solution 311 or container 310 within the acceptable storage temperature value range. Alternatively, the container 310 and/or solution 311 may be discarded as the solution 311 may no longer be fit for use based on the temperature value falling outside the acceptable temperature value range. As another example if a first receiver 330 receives a temperature value that is within an acceptable use temperature value range, the receiver 330 may provide an alert to a user or to a system configured to receive such alerts. Based on the alert, a user or system may determine that the solution 311 can be used as the temperature of the solution is within the acceptable use temperature value range.

As another example, if a second receiver 340 receives a pH value that is outside an acceptable pH value range, the receiver 340 may provide an alert to a user or to a system configured to receive such alerts. Based on the alert, a user or system may evaluate the container 310 to make a determination regarding the cause of the pH value being outside the acceptable pH value range. Based on the determination, the container 310 and solution 311 may be preserved. Alternatively, the container 310 and/or solution 311 may be discarded as the pH value based alert may indicate a solution leak, rendering the container 310 and solution 311 unusable.

As another example implantation of the techniques disclosed herein, the configuration of FIG. 3 may be used to transmit updates to a temperature and pH value. The standalone device 350 may periodically provide a magnetic field to NFC tag 320 and NFC tag 320 may determine a temperature value and pH value in accordance with the techniques disclosed herein. The NFC tag 320 may contain a storage that stores previously determined temperature and pH values. The NFC tag 320 may determine if a newly measured temperature value and/or pH value is different than the previously determined temperature value and/or pH value. The NFC tag 320 may transmit the temperature value and/or pH value only if the respective value is different a previously obtained value such that the NFC tag 320 transmits a temperature value and/or pH value if there is a change in temperature or pH. Notably, a change in pH may correspond to the presence of solution 311 outside the enclosure of the container 310, indicating a leak or a spill.

Although features and elements are described above in particular combinations, one of ordinary skill in the art will appreciate that each feature or element can be used alone or in any combination with the other features and elements. In addition, the methods described herein may be implemented in a computer program, software, or firmware incorporated in a computer-readable medium for execution by a computer or processor. Examples of computer-readable media include electronic signals (transmitted over wired or wireless connections) and computer-readable storage media. Examples of computer-readable storage media include, but are not limited to, a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

What is claimed:
1. A method comprising:
receiving a magnetic field at a near field communication (NFC) tag;
generating energy via induction from the magnetic field;
activating a temperature sensor from at least a portion of the generated energy;
activating an electrochemical sensor;
measuring a temperature value of one of a container and a solution based on thermal conduction, wherein the temperature value is measured using a temperature sensor;
measuring a pH value, wherein the pH value is measured using an electrochemical sensor;
transmitting the temperature value to a first receiver using at least a portion of the generated energy; and
transmitting the pH value to a second receiver using at least a portion of the generated energy.
2. The method of claim 1, wherein the first receiver and the second receiver are the same.
3. The method of claim 1 further comprising determining a presence of one of a condensation and a solution, by the electrochemical sensor.
4. The method of claim 3, wherein the pH value of the solution is transmitted if presence of the solution is detected.
5. The method of claim 1 further comprising generating an alert if the temperature value falls outside an acceptable storage state temperature range.
6. The method of claim 1 further comprising generating an alert if the temperature value falls within an acceptable use temperature range.
7. The method of claim 1, further comprising:
transmitting the temperature value from the first receiver via one of a Wi-Fi, an infrared, a cellular, and a Bluetooth format; and
transmitting the pH value from the second receiver via one of a Wi-Fi, an infrared, a cellular, and a Bluetooth format.
8. The method of claim 1, further comprising securing the NFC tag to the container using a securing component wherein the securing component is one of an adhesive, a binding tape, a suction element, and a mechanical connection.
9. The method of claim 1, further comprising receiving a ready indication at the first receiver based on the temperature value meeting a ready threshold.

10. The method of claim 1, further comprising receiving a warning indication at the second receiver based on the pH value meeting a warning threshold.

11. A Near Field Communications (NFC) tag device, comprising:
a housing;
a temperature sensor at least partially contained in the housing and configured to measure a temperature value of one of a container, a solution, and the housing, wherein the temperature sensor measures the temperature value based on thermal conduction; and
an electrochemical sensor at least partially contained in the housing and configured to measure a pH value;
wherein the NFC tag is configured to transmit a temperature signal to a first receiver, the temperature signal comprising the temperature value; and
wherein the NFC tag is configured to transmit a pH signal to a second receiver, the pH signal comprising the pH value.

12. The device of claim 11 further comprising an antenna configured to generate energy via a received magnetic field.

13. The device of claim 11, wherein the first receiver and the second receiver are the same.

14. The device of claim 11, wherein the electrochemical sensor is further configured to detect whether it senses either condensation or the solution.

15. The device of claim 14, wherein the electrochemical sensor is further configured to transmit the pH signal if it detects that it senses the solution.

16. The device of claim 14 further configured to transmit the temperature value if the temperature value falls outside an acceptable storage state temperature range.

17. The device of claim 11, wherein the housing comprises a flexible laminate.

18. The device of claim 11, wherein the NFC tag is configured to transmit the temperature signal and the pH signal using energy generated from electromagnetic induction.

19. The device of claim 11, further comprising a securing component configured to secure the NFC tag to the container, wherein the securing component is one of an adhesive, a binding tape, a suction element, and a mechanical connection.

20. The device of claim 11, further comprising a passive storage configured to store one of a manufacturing parameter, a drug parameter, a production date, an expiration date, a prior temperature value, a lot number, and a date of last use.

* * * * *